US010874376B2

(12) United States Patent
Waldstreicher et al.

(10) Patent No.: US 10,874,376 B2
(45) Date of Patent: Dec. 29, 2020

(54) ENDOBRONCHIAL CATHETER

(71) Applicant: Biosense Webster (Israel) Ltd., Yokneam (IL)

(72) Inventors: Jonathan Reuben Waldstreicher, West Orange, NJ (US); William Sanford Krimsky, Bel Air, MD (US); Yitzhack Schwartz, Haifa (IL); Avi Shalgi, Haifa (IL); Meir Bar-Tal, Haifa (IL); Matityahu Amit, Zur-Yigal (IL); Gal Hayam, Tivon (IL); Refael Itah, Tel-Aviv (IL); Robert D. Ainsworth, Scotts Valley, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 127 days.

(21) Appl. No.: 15/409,111

(22) Filed: Jan. 18, 2017

(65) Prior Publication Data
US 2017/0128039 A1    May 11, 2017

Related U.S. Application Data

(62) Division of application No. 13/890,294, filed on May 9, 2013.
(Continued)

(51) Int. Cl.
*A61B 8/12* (2006.01)
*A61B 10/02* (2006.01)
(Continued)

(52) U.S. Cl.
CPC .............. *A61B 8/12* (2013.01); *A61B 5/0036* (2018.08); *A61B 5/0538* (2013.01); *A61B 5/062* (2013.01);
(Continued)

(58) Field of Classification Search
CPC ...... A61M 25/0082; A61M 2025/1052; A61M 25/04; A61B 10/04; A61B 5/062;
(Continued)

(56) References Cited

U.S. PATENT DOCUMENTS

| 6,554,851 B1 | 4/2003 | Palasis et al. |
| 6,788,967 B2 | 9/2004 | Ben-Haim et al. |

(Continued)

FOREIGN PATENT DOCUMENTS

| CN | 1168628 A | 12/1997 |
| JP | 2003-534037 A | 11/2003 |

(Continued)

OTHER PUBLICATIONS

U.S. Appl. No. 13/890,294.
(Continued)

*Primary Examiner* — Amanda Lauritzen Moher
*Assistant Examiner* — Katherine M McDonald
(74) *Attorney, Agent, or Firm* — Frost Brown Todd LLC

(57) ABSTRACT

An endobronchial probe includes a deflector having a bore extending therethrough at an angle to its long axis for passage of a tool. The probe includes a location sensor and an ultrasound imager. A push-pull anchoring system comprises a plurality of guides and wires that can extend beyond the guides and retract within the guides. When extended the wires diverge from the long axis sufficiently to engage a bronchus. The probe includes a balloon disposed on the distal segment contralateral to bore that when inflated urges the mouth of the bore into contact with the bronchial wall.

9 Claims, 8 Drawing Sheets

Related U.S. Application Data

(60) Provisional application No. 61/650,615, filed on May 23, 2012.

(51) Int. Cl.

| | | |
|---|---|---|
| *A61B 10/04* | (2006.01) | |
| *A61B 8/00* | (2006.01) | |
| *A61B 18/14* | (2006.01) | |
| *A61B 8/08* | (2006.01) | |
| *A61M 25/00* | (2006.01) | |
| *A61B 5/00* | (2006.01) | |
| *A61B 5/06* | (2006.01) | |
| A61B 18/00 | (2006.01) | |
| A61M 25/10 | (2013.01) | |
| A61M 25/04 | (2006.01) | |
| A61B 17/00 | (2006.01) | |
| A61B 17/34 | (2006.01) | |
| A61B 34/20 | (2016.01) | |
| A61B 90/00 | (2016.01) | |

(52) U.S. Cl.
CPC ........... *A61B 5/063* (2013.01); *A61B 5/4836* (2013.01); *A61B 8/08* (2013.01); *A61B 8/0841* (2013.01); *A61B 8/4254* (2013.01); *A61B 8/4263* (2013.01); *A61B 8/445* (2013.01); *A61B 8/463* (2013.01); *A61B 10/0233* (2013.01); *A61B 10/04* (2013.01); *A61B 18/1477* (2013.01); *A61B 18/1492* (2013.01); *A61M 25/0082* (2013.01); *A61B 5/6853* (2013.01); *A61B 2010/045* (2013.01); *A61B 2017/0065* (2013.01); *A61B 2017/00809* (2013.01); *A61B 2017/3488* (2013.01); *A61B 2018/00011* (2013.01); *A61B 2018/00273* (2013.01); *A61B 2018/00285* (2013.01); *A61B 2018/00541* (2013.01); *A61B 2018/00839* (2013.01); *A61B 2018/00988* (2013.01); *A61B 2018/1475* (2013.01); *A61B 2034/2051* (2016.02); *A61B 2090/3784* (2016.02); *A61B 2090/3908* (2016.02); *A61M 25/04* (2013.01); *A61M 2025/1052* (2013.01)

(58) Field of Classification Search
CPC ......... A61B 5/063; A61B 8/12; A61B 5/0036; A61B 8/4263; A61B 8/445; A61B 8/4254; A61B 18/1492; A61B 5/0538; A61B 5/4836; A61B 8/0841; A61B 18/1477; A61B 8/08; A61B 8/463; A61B 10/0233; A61B 5/6853; A61B 2010/045; A61B 2017/00809; A61B 2017/3488; A61B 2018/00839; A61B 2018/00011; A61B 2018/00273; A61B 2034/2051; A61B 2090/3784; A61B 2090/3908; A61B 2017/0065; A61B 2018/00988; A61B 2018/00285; A61B 2018/00541; A61B 2018/1475

See application file for complete search history.

(56) References Cited

U.S. PATENT DOCUMENTS

| | | | |
|---|---|---|---|
| 6,814,733 | B2 | 11/2004 | Schwartz |
| 6,997,924 | B2 | 2/2006 | Schwartz et al. |
| 7,156,816 | B2 | 1/2007 | Schwartz et al. |
| 7,451,765 | B2 | 11/2008 | Adler |
| 7,536,218 | B2 | 5/2009 | Govari et al. |
| 7,674,250 | B2 | 3/2010 | Freyman et al. |
| 7,756,576 | B2 | 7/2010 | Levin |
| 8,147,413 | B2 | 4/2012 | Abraham |
| 8,821,376 | B2 | 9/2014 | Tolkowsky |
| 8,932,207 | B2 | 1/2015 | Greenburg et al. |
| 9,204,819 | B2 | 12/2015 | Grunwald et al. |
| 2006/0206056 | A1 | 9/2006 | Freyman et al. |
| 2007/0038089 | A1 | 2/2007 | Hatano et al. |
| 2007/0049817 | A1 | 3/2007 | Preiss et al. |
| 2007/0260217 | A1* | 11/2007 | Von Oepen ............ A61F 2/954 604/509 |
| 2008/0051756 | A1* | 2/2008 | Makower .......... A61M 25/0084 604/508 |
| 2008/0167639 | A1 | 7/2008 | Gilboa |
| 2010/0063392 | A1 | 3/2010 | Nishina et al. |
| 2010/0076303 | A1 | 3/2010 | McKinley |
| 2010/0198192 | A1* | 8/2010 | Serina ................ A61B 1/00078 604/523 |
| 2010/0241028 | A1 | 9/2010 | Johnson et al. |
| 2011/0112527 | A1 | 5/2011 | Hamilton, Jr. et al. |
| 2012/0053485 | A1* | 3/2012 | Bloom ............... A61B 1/00082 600/567 |
| 2013/0317339 | A1 | 11/2013 | Waldstreicher et al. |
| 2014/0107478 | A1* | 4/2014 | Seward ............ A61M 25/1002 600/431 |

FOREIGN PATENT DOCUMENTS

| | | |
|---|---|---|
| JP | 2004-502562 A | 1/2004 |
| JP | 2009-056238 A | 3/2009 |
| JP | 2009-254837 A | 11/2009 |
| JP | 2011-519699 A | 7/2011 |
| JP | 2013-176559 A | 9/2013 |
| WO | WO 2008/046031 A2 | 4/2008 |

OTHER PUBLICATIONS

Gavrielides, Ph.D., M.A., et al., "Noncalcified Lung Nodules: Volumetric Assessment with Thoracic CT," Radiology, Apr. 2009, 251(1):26-37, 12 pgs.
Mozley, P.D., et al., "Measurement of Tumor Volumes Improves RECIST-Based Response Assessments in Advanced Lung Cancer," Translational Oncology, Feb. 2012, 5(1):19-25, 7 pgs.
Snoeren, N., et al., "Viable Tumor Tissue Adherent to Needle Applicators after Local Ablation: A Risk Factor for Local Tumor Progression," Annals of Surgical Oncology, Dec. 2011, 18(13):3702-3710, 9 pgs.
Australian Office Action, Examination report No. 1 for standard patent application, dated Sep. 6, 2017 for Application No. AU 2013205887, 4 pgs.
Australian Office Action, Examination report No. 2 for standard patent application, dated Apr. 11, 2018 for Application No. AU 2013205887, 2 pgs.
Chinese Office Action, First Office Action, dated Oct. 29, 2015 for Application No. CN 201310195021.9, 4 pgs.
Chinese Office Action, The Second Office Action, dated Jul. 8, 2016 for Application No. CN 201310195021.9, 10 pgs.
Chinese Search Report dated Jun. 30, 2016 for Application No. CN 201310195021.9, 3 pgs.
European Search Report, Partial, dated Aug. 27, 2014 for Application No. EP 13169004.2, 7 pgs.
European Search Report, Extended, and Written Opinion dated Jan. 20, 2015 for Application No. EP 13169004.2, 11 pgs.
Japanese Office Action, Notification of Reasons for Refusal, dated Mar. 28, 2017 for Application No. JP 2013-107850, 2 pgs.
Japaese Office Action, Notification of Reasons for Refusal, dated Jun. 26, 2018 for Application No. JP 2017-166649, 4 pgs.
U.S. Appl. No. 61/650,615, filed May 23, 2012.
Japanese Office Action dated Oct. 2, 2018 for Application No. 2017-166649, 3 pages.

* cited by examiner

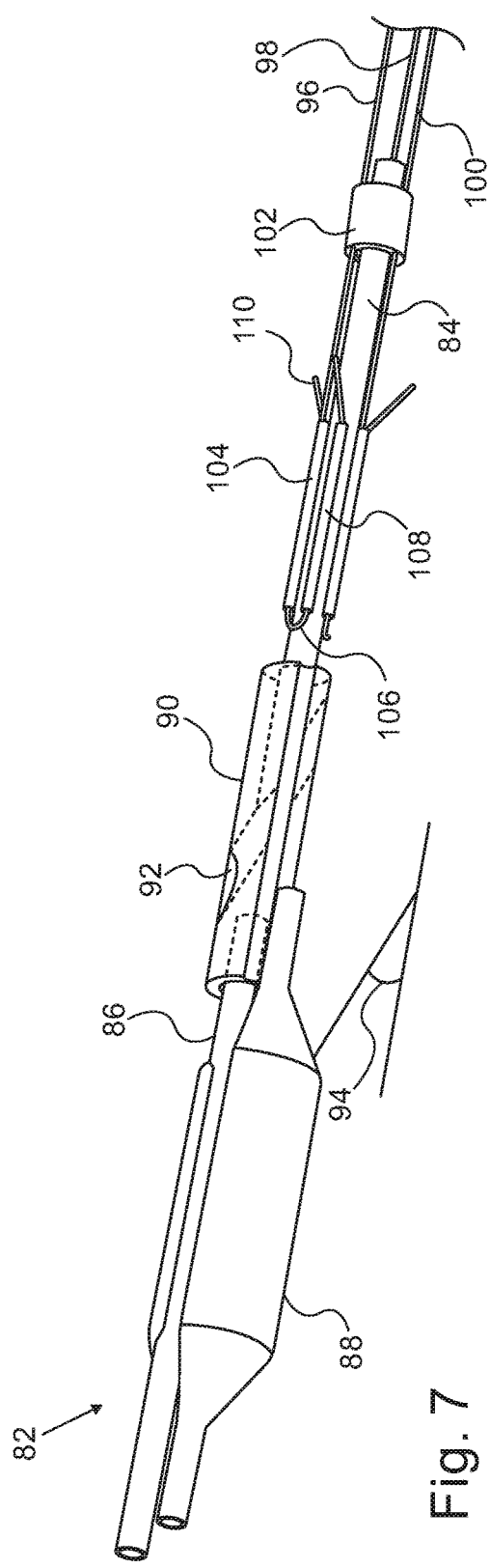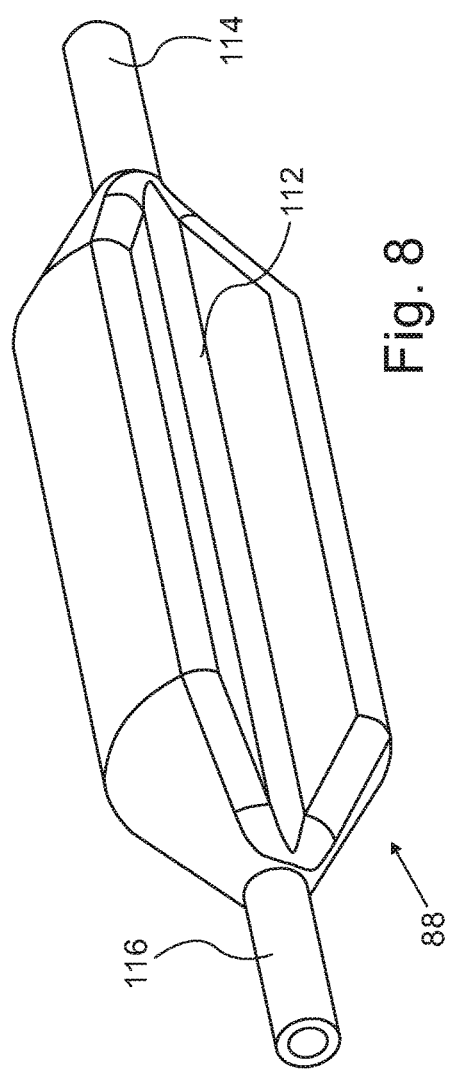
Fig. 7
Fig. 8

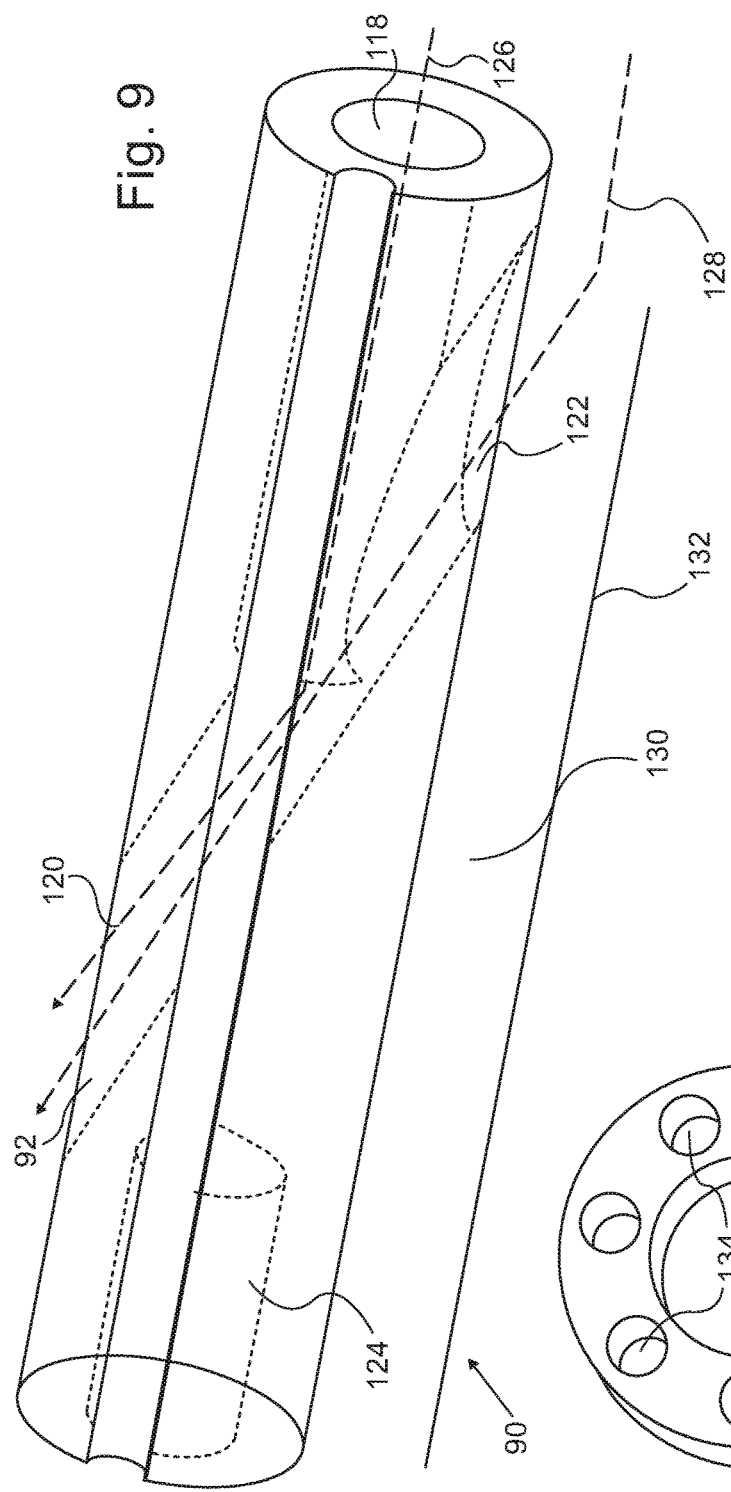
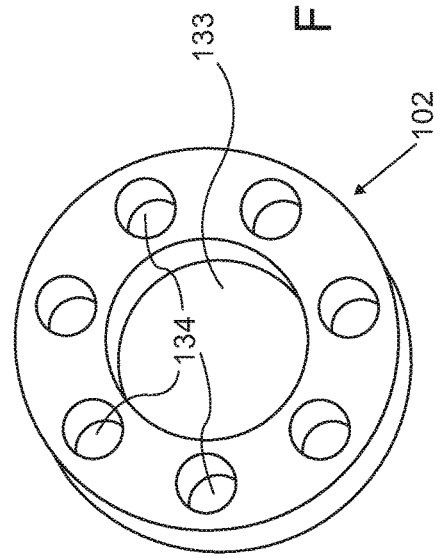

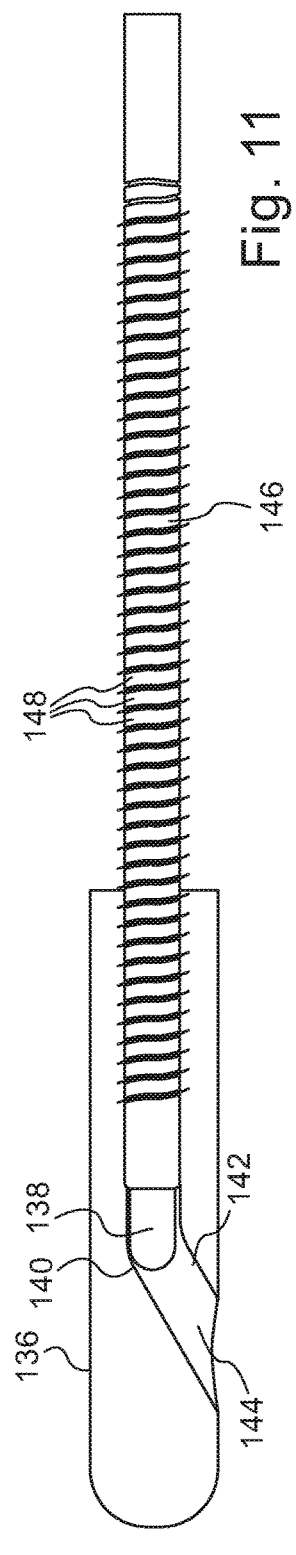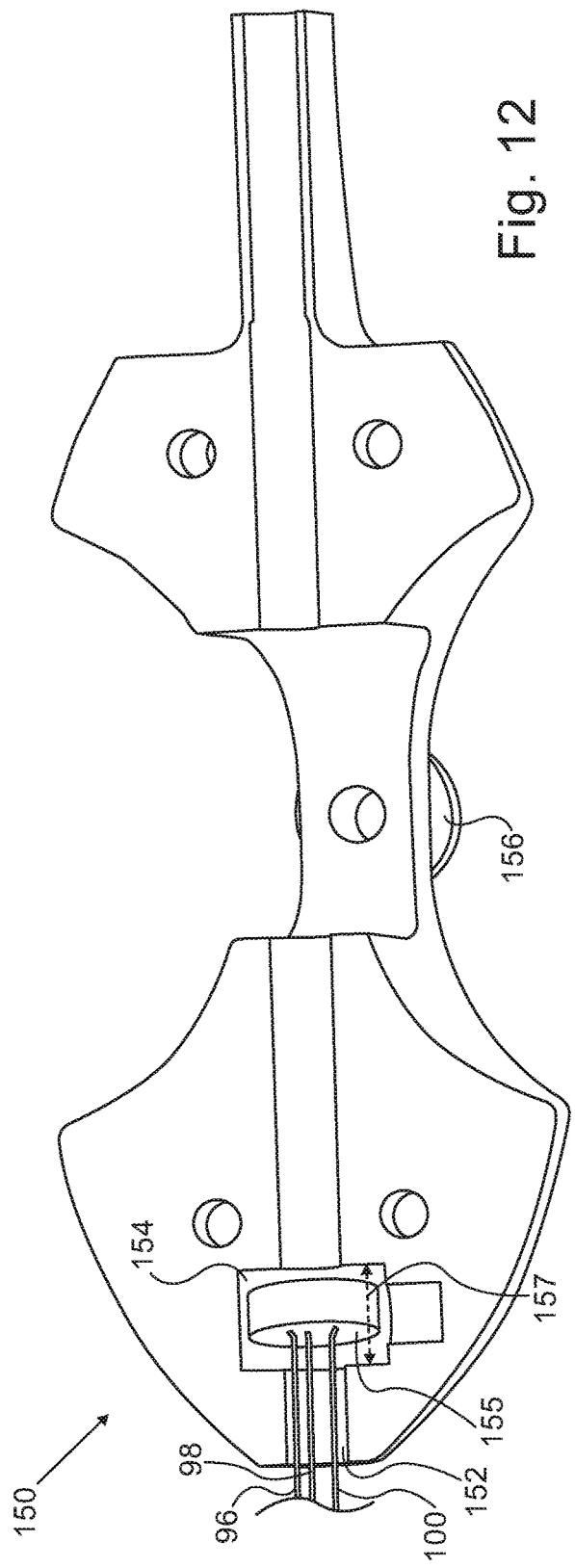

ENDOBRONCHIAL CATHETER

CROSS-REFERENCE TO RELATED APPLICATIONS

This Application is a divisional of U.S. patent application Ser. No. 13/890,294, filed on May 9, 2013, now abandoned, which claims the benefit of U.S. Provisional Application No. 61/650,615, filed May 23, 2012, the entirety of these applications being incorporated herein by reference thereto.

BACKGROUND OF THE INVENTION

1. Field of the Invention

This invention relates to tissue ablation systems. More particularly, this invention relates to improvements in an endobronchial catheter.

2. Description of the Related Art

In a medical procedure which typically has as its last stage ablation of a cancerous lesion in a lung, there are a number of preliminary stages. A typical scenario includes first imaging the lesion, for example by anatomic imaging with a computerized tomography (CT) scan, and/or by metabolic imaging with a PET (positron emission tomography)—CT scan. Subsequent stages of the overall procedure comprise insertion of a bronchoscope to inspect the lesion, performing a biopsy of the lesion, and then ablating the lesion. The multiplicity of subsequent stages typically are performed on the patient in succession, as if they were separate sessions.

McKinley, U.S. Patent Application Publication No. 2010/0076303, now abandoned, describes a probe or catheter, usable with a navigation system, which includes a longitudinal lumen that curves outwardly through a sidewall prior to reaching a distal tip of the probe. The distal tip contains a position sensor as part of the navigation system. The lumen provides a working channel that guides a tool into a sidewall of a branched structure.

SUMMARY OF THE INVENTION

There is provided according to embodiments of the invention an endoscopic apparatus including an elongated assembly having a lumen extending generally along its long axis. A deflector is disposed in the distal segment and has a bore extending therethrough at an angle to the long axis. The bore has an exit pore and a sideward communication with the lumen. The lumen, the bore and the sideward communication are dimensioned to accept passage of a tool therethrough. A location sensor is disposed in the distal segment. The location sensor is connectable to a position processor that is operative for computing a location of the distal segment responsively to signals from the location sensor. An ultrasound imager is disposed in the distal segment, and is connectable to electronic circuitry for processing data provided by the ultrasound imager. A push-pull anchoring system includes a plurality of guides and respective wires threaded therethrough. The wires are moveable between a first position, wherein the wires are retracted within the guides, and a second position, wherein the wires extend beyond the guides and diverge from the long axis sufficiently to engage a bronchus when the assembly is inserted therein. The apparatus includes an inflatable balloon disposed on the distal segment contralateral to the exit pore.

According to an aspect of the apparatus, the assembly has another lumen and the deflector has an entrance pore that communicates with the other lumen, wherein the bore of the deflector leads to the entrance pore and accepts passage of the tool from the other lumen through the entrance pore and through the exit pore.

An additional aspect of the apparatus includes a proximally located control handle, wherein the anchoring system is disposed between the deflector and the control handle, and the wires are controlled from the control handle.

According to one aspect of the apparatus, in the second position, the wires extend outward from the long axis in a generally proximal direction.

According to still another aspect of the apparatus, the location sensor is a tri-axial magnetic field sensor.

According to yet another aspect of the apparatus, the location sensor is an electrode that reports impedance measurement signals to the position processor cooperatively with a plurality of body surface electrodes.

A further aspect of the apparatus includes a retractable biopsy needle and at least one retractable ablation needle, the biopsy needle and the ablation needle is deployable via the deflector.

There is further provided according to embodiments of the invention an endoscopic apparatus having a proximal segment, a distal segment and a distal end configured to penetrate into a lung. The apparatus includes a location sensor in the distal segment, configured to generate a signal indicative of a location with respect to the lung, an ultrasound imager, configured to image the lung, a retractable biopsy needle, configured to aspirate a sample of the lung after deployment of the biopsy needle, and at least one retractable ablation needle, configured to ablate a section of the lung after deployment of the at least one ablation needle.

An aspect of the apparatus includes a balloon configured to surround a portion of the distal segment, and, upon inflation of the balloon, is operative to seal the section of the lung.

According to an additional aspect of the apparatus, the biopsy needle is configured to apply a sealant to a sampled portion of the lung.

According to one aspect of the apparatus, the ablation needle is configured to apply a sealant to an ablated portion of the lung after ablation therewith.

There is further provided according to embodiments of the invention a method of endoscopy, which is carried out by inserting into a bronchus of a lung an elongated assembly having a lumen, a long axis, a distal segment and a deflector disposed in the distal segment. The method is further carried out by introducing a tool into the deflector, the deflector having a bore extending therethrough at an angle to the long axis. The bore has an exit pore and a sideward communication with the lumen. The method is further carried out by transmitting signals from a location sensor disposed in the distal segment to a position processor that is operative for computing a location of the distal segment responsively to the signals from the location sensor, imaging a target in the lung using an ultrasound imager disposed in the distal segment and transmitting data provided by the ultrasound imager to electronic circuitry for processing thereof, and urging the exit pore of the deflector against a wall of the bronchus by inflating an inflatable balloon disposed on the distal segment contralateral to the exit pore. The method is further carried out by thereafter penetrating the wall of the bronchus with the tool via the exit pore to reach the target in the lung with the tool, anchoring the assembly to provide counter-traction thereon while penetrating the wall of the bronchus using a push-pull anchoring system. The anchoring system includes a plurality of guides and respective wires threaded therethrough and is operated by moving the wires between a first position wherein the wires are retracted within the guides and a second position wherein the wires extend beyond the guides and diverge from the long axis sufficiently to engage the wall of the bronchus. The method is further carried out by performing an operation on the target using the tool.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein:

FIG. 7 is a partial view of an assembly of an endobronchial probe in accordance with an alternate embodiment of the invention;

FIG. 8 is a perspective view of a balloon in the assembly shown in FIG. 7 in accordance with an embodiment of the invention;

FIG. 9 is a partially schematic elevation of a deflector in the assembly shown in FIG. 7, shown in slight perspective in accordance with an embodiment of the invention;

FIG. 10 is an end view of a cylindrical guide member in the assembly shown in FIG. 7, shown in slight perspective in accordance with an embodiment of the invention;

FIG. 11 is a schematic sectional view of another deflector with a dilator inserted therein in accordance with an embodiment of the invention;

FIG. 12 is an elevation of a top plate of a handle of an endobronchial probe in accordance with an embodiment of the invention;

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Aspects of the present invention may be embodied in software programming code, which is typically maintained in permanent storage, such as a computer readable medium. In a client/server environment, such software programming code may be stored on a client or a server. The software programming code may be embodied on any of a variety of known non-transitory media for use with a data processing system, such as a diskette, hard drive, electronic media or CD-ROM. The code may be distributed on such media, or may be distributed to users from the memory or storage of one computer system over a network of some type to storage devices on other computer systems for use by users of such other systems.

Figure 1:
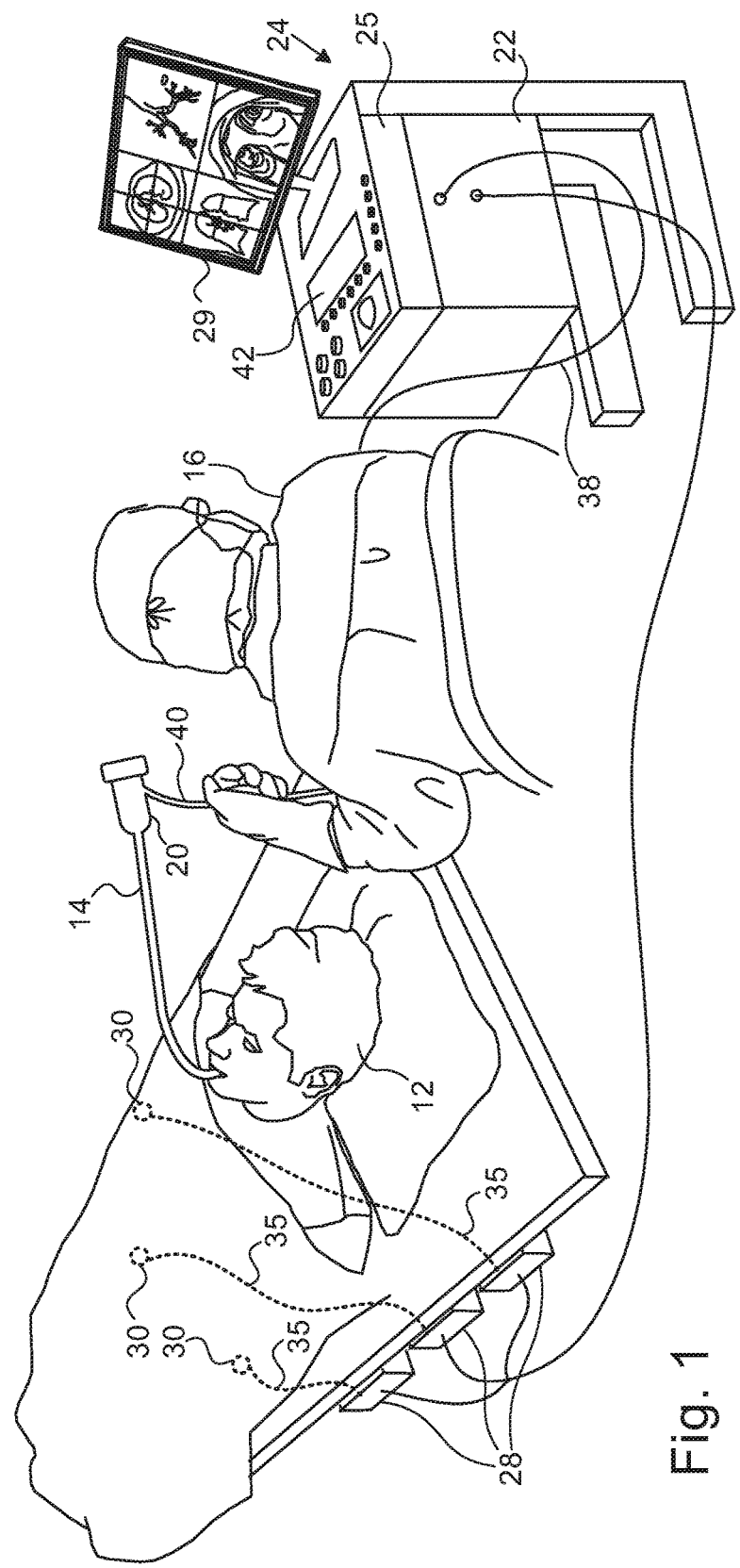
FIG. 1 is a pictorial illustration of a system for performing bronchoscopy and ablative procedures on a living subject, which is constructed and operative in accordance with an embodiment of the invention.

Turning now to the drawings, reference is initially made to FIG. 1, which is a pictorial illustration of a system 10 for performing bronchoscopy and ablative procedures on the lower respiratory system of a living subject 12, which is constructed and operative in accordance with a disclosed embodiment of the invention. The system comprises a flexible endobronchial probe 14, which is inserted by an operator 16 through the trachea into the bronchial tree of the subject 12. The operator 16, who is typically a physician, brings the catheter's distal tip (not shown) into contact with the bronchial wall at an ablation target site. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein. Moreover, while the principles of the invention are disclosed with respect to an endobronchial probe, they may be applied to endoscopic probes having medical applications in sites other than the bronchial tree.

Areas determined to be abnormal, for example by evaluation of the images and visual appearance through the endobronchial probe 14, can be ablated by application of thermal energy, e.g., by passage of radiofrequency electrical current through wires in the catheter to one or more electrodes at or extending from the distal tip, which apply the radiofrequency energy to the target lesion, typically found in lung parenchyma or a lymph node. The energy is absorbed in the tissue, heating it to a point (typically about 50-90° C.) at which it becomes inviable.

The endobronchial probe 14 typically comprises a handle 20, having suitable controls on the handle to enable the operator 16 to steer, position and orient the distal end of the catheter as desired for the ablation and to control an anchoring system described in further detail below. To aid the operator 16, several other components are included in the endobronchial probe 14, which are described in more detail below. The distal portion of the endobronchial probe 14 contains location sensors that provide signals to a position processor 22, located in a console 24. The target site can be located with the aid of an ultrasound imager at or near the distal end of the endobronchial probe 14. Suitable electronic circuitry for processing data provided by the ultrasound imager is located in the console 24.

Ablation energy and electrical signals can be conveyed to and from electrodes at the distal end of the endobronchial probe 14 through one or more ablation electrodes that can be positioned at or near the distal tip of the endobronchial probe 14 via cable 38 to the console 24. The ablation electrodes may be realized as a retractable needle or a probe or wire guided through the needle. Other control signals may be conveyed from the console 24 through the cable 38 to the electrodes. Various sensors or electrodes to detect and measure physical characteristics of the environment may also be connected to the console 24, and may be disposed in the distal portion of the endobronchial probe 14 with connections via the cable 38.

Wire connections 35 link the console 24 with body surface electrodes 30 and other components of a positioning sub-system, which may include an electrode disposed near the tip of the endobronchial probe 14. The body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near the ablation needle or other ablation electrode.

The console 24 typically contains one or more ablation power generators 25. The endobronchial probe 14 may be adapted to conduct ablative energy to the target tissue using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

The position processor 22 is an element of a positioning subsystem in the system 10 that measures location and orientation coordinates of the distal portion of the endobronchial probe 14.

In one embodiment, the positioning subsystem comprises a magnetic position tracking arrangement that determines the position and orientation of the endobronchial probe 14 by generating magnetic fields in a predefined working volume and sensing these fields at the catheter, using field generating coils 28. The positioning subsystem may employ impedance measurement, as taught, for example in U.S. Pat. No. 7,756,576, which is hereby incorporated by reference, and in the above-noted U.S. Pat. No. 7,536,218.

As noted above, the endobronchial probe 14 is coupled to the console 24, which enables the operator 16 to observe and regulate the functions of the endobronchial probe 14. A fiberoptic conduit 40 transmits light through the endobronchial probe 14 from a source (not shown) in the console 24, which illuminates the tracheobronchial structures of the subject 12. The console 24 includes a processor, preferably a computer with appropriate signal processing circuits. The processor is coupled to drive a display monitor 29, which can show views and images acquired by various modalities, e.g., the conduit 40. The signal processing circuits typically receive, amplify, filter and digitize signals from the endobronchial probe 14, including signals generated by the above-noted sensors and a plurality of location sensing electrodes (not shown) that are optionally located distally in the endobronchial probe 14. The digitized signals are received and used by the console 24 and the positioning system to compute the position and orientation of the endobronchial probe 14 and to analyze the electrical signals from the electrodes. An endobronchial probe configured to perform the multiple functions herein described is sometimes known as a "compound endobronchoscope".

The system 10 may include an electrocardiogram (ECG) monitor 42, coupled to receive signals from one or more body surface electrodes. Conventional pumps and hydraulic lines (not shown) for circulating liquids through the endobronchial probe 14 for cooling the ablation site may be provided.

Figure 2:
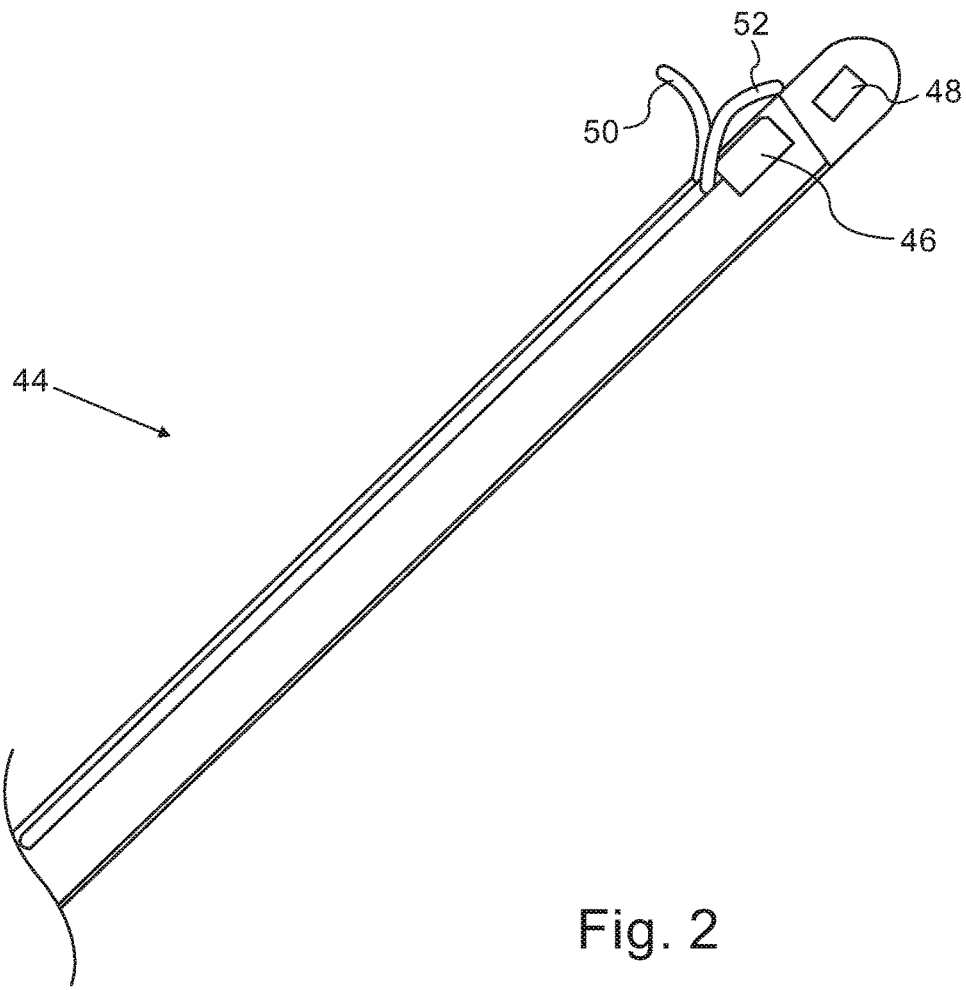
FIG. 2 is a schematic elevation of a distal segment of an endobronchial probe in accordance with an embodiment of the invention.

Embodiments of the present invention provide the possibility of performing all the stages noted above in a single "all-in-one" minimally invasive procedure through the mouth of the subject. Reference is now made to FIG. 2, which is a schematic elevation of a distal segment 44 of an endobronchial probe in accordance with an embodiment of the invention. The distal segment 44 which at its distal end has an ultrasound imager 46 and a location sensor 48. The location sensor 48 could comprise a sensor such as the tri-axial magnetic field sensor provided in the above-noted CARTO 3 System. With the tri-axial sensor, this system can determine the position of the distal segment 44 with six degrees of freedom. Alternatively, the location sensor 48 may comprise an electrode for measuring impedance cooperatively with the body surface electrodes 30 (FIG. 1) as taught in the above-noted U.S. Pat. No. 7,536,218.

In addition the distal segment 44 contains a retractable aspiration or biopsy needle 50, and at least one retractable ablation needle 52. The biopsy needle 50 may be used to perform aspiration or core biopsies. In some embodiments, the biopsy needle 50 may be used for ablation and for performing a biopsy. For simplicity, only one retractable ablation needle 52 is shown in the figure. However, some embodiments may comprise more than one such needle. Embodiments with more than one retractable ablation needle may be indicated for cases where a lesion to be ablated is large.

Typically, all the above-described elements incorporated into the distal segment 44 are operated by a physician using respective controls at the proximal end of the endobronchial probe. The controls may be coupled to their respective distal elements by any method known in the art, including, but not limited to, one or more of mechanical, electrical, ultrasound, and/or optical coupling. For simplicity and clarity, such controls are not shown in the figures.

The description herein assumes that the probe is operated manually, using the controls described above. However, it will be appreciated that the probe may be operated in a fully robotic mode, by application of appropriate instrumentation.

The following description assumes that the stages described above are performed in the order given above, i.e., inspection, biopsy, and then ablation. Those having ordinary skill in the art will be able to adapt the description, *Mutatis mutandis*, to encompass other orders for the stages, as well as to encompass other functions of the probe described below.

The following describes the use of the endobronchial probe 14 (FIG. 1) during the imaging stage of a procedure, according to an embodiment of the present invention. It will be understood that this imaging stage may be applied at will at any required period during the whole procedure, including at the beginning of the procedure.

Figure 3:
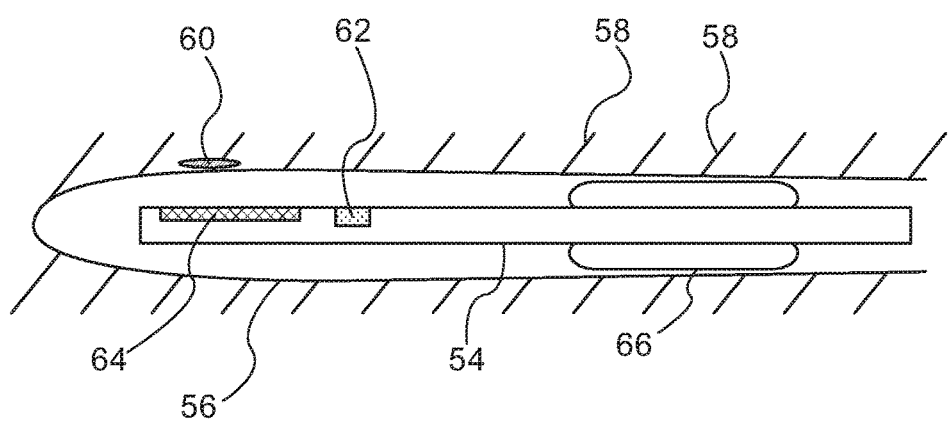
FIG. 3 is a schematic diagram of a distal segment of an endobronchial probe, which has been deployed through a conventional endobronchoscope in accordance with an embodiment of the invention.

Reference is now made to FIG. 3, which is a schematic diagram of a distal segment of a probe 54 which may have been deployed through a conventional endobronchoscope, and which has been positioned within the lumen of a bronchus 56, in accordance with an embodiment of the invention. Peribronchial lung parenchyma is represented by diagonal lines, e.g., diagonal lines 58. The probe 54 is inserted into a section of the lung, into proximity with a target 60. In this example the target 60 is extrabronchial. However, intrabronchial lesions may also be managed. The insertion of the probe 54 is typically via the working channel of a standard bronchoscope, and the procedure performed with the probe may be accomplished within and/or adjacent to the bronchoscope. The probe 54 may be introduced under direct vision, without using a conventional bronchoscope.

Typical lung targets include, but are not limited to lesions such as suspected or confirmed neoplasms, lymph nodes, and arteriovenous malformations. For simplicity, in the following description the lung target is assumed to comprise a nodular lesion. A location sensor 62 in the probe 54 enables tracking of the distal end of the probe 54, so that insertion to the correct region of the lung is possible, and may be assisted by an ultrasound imager 64. During the insertion, the probe is sheathed by a deflated balloon 66. Typically the balloon 66 is located 1-3 cm proximal to the ultrasound imager 64.

Figure 4:
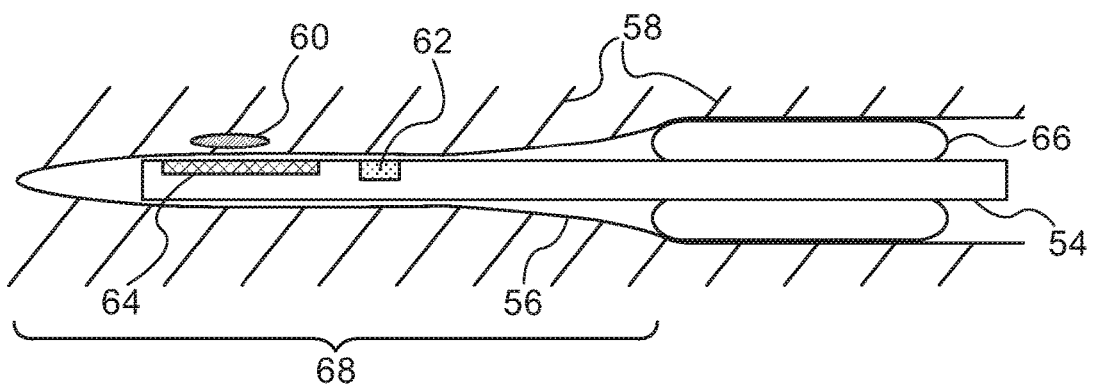
FIG. 4 is a schematic diagram of the probe shown in FIG. 3, which is positioned within the lumen of a bronchus in accordance with an embodiment of the invention.

Reference is now made to FIG. 4, which is a schematic diagram of the probe 54 that has been determined to have been correctly positioned within the lumen of the bronchus 56, in accordance with an embodiment of the invention. As shown in FIG. 4, once correctly positioned, the balloon 66 is inflated to seal and isolate a distal portion 68 of the bronchus from the remainder of the tracheobronchial tree. The isolation allows the lung supplied by the distal portion 68 to collapse, thereby bringing the target 60 closer to the ultrasound imager 64, enabling the ultrasound imager 64 to provide a better image than would be generated from an uncollapsed lung. Moreover, collapse of the lung allows the RF ablation zone to increase in size for a given power output as the RF energy need not be conducted through air. In some embodiments the ultrasound imager 64 is configured to perform acoustic radiation force impulse imaging (ARFI), typically of the lung section that is isolated by inflation of the balloon 66.

Figure 5:
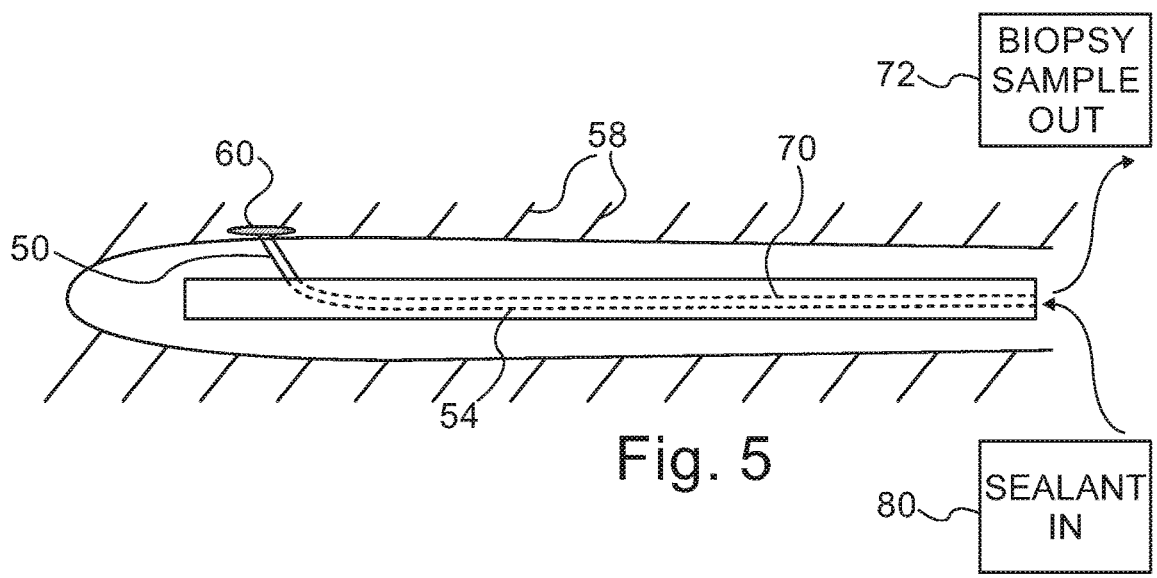
FIG. 5 is a schematic diagram of the probe shown in FIG. 4, illustrating deployment of a biopsy needle, in accordance with an embodiment of the invention.

Reference is now made to FIG. 5, which is a schematic diagram of the probe 54, illustrating deployment of the biopsy needle 50, in accordance with an embodiment of the invention. Once the probe 54 is positioned correctly, the biopsy needle 50 may be deployed by insertion of tubing 70 through the probe 54. During deployment the lung supplied by the distal portion 68 (FIG. 4) may be either collapsed or expanded. After deployment, the operator navigates the biopsy needle 50 into the target 60, aspirating a sample 72 from the target 60 through the tubing 70 for evaluation. Sealant may be introduced through the tubing 70 as necessary, as described in more detail hereinbelow. Assuming that the evaluation shows that the target 60 is cancerous the biopsy needle 50 is retracted and the ablation needle 52 (FIG. 2) is deployed to contact the target 60 as described below.

Figure 6:
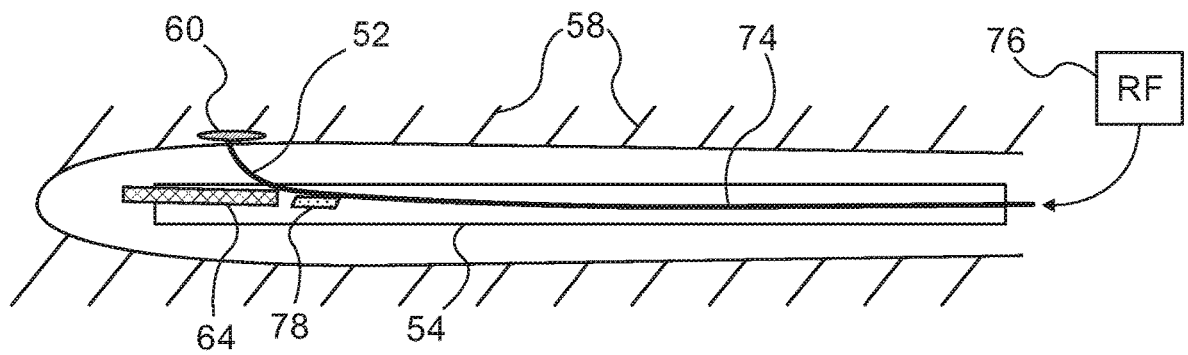
FIG. 6 is a schematic diagram of the probe shown in FIG. 4, illustrating deployment of an ablation needle in accordance with an embodiment of the invention.

Reference is now made to FIG. 6, which is a schematic diagram of the probe 54, illustrating deployment of the ablation needle 52 by insertion using an electrically conductive wire 74, in accordance with an embodiment of the invention. Contact of the ablation needle 52 with a desired location of the target 60 can be confirmed by the image generated by the ultrasound imager 64, and once confirmed, the target 60 can be ablated using the ablation needle 52. The ablation is herein assumed to be by injection of radiofrequency energy (indicated by a functional block 76) into the lesion. However, other ablation modalities, such as, but not limited to, injection of laser, microwave, or high frequency ultrasound energy, or the application of electroporation, may be used. The ablation needle 52 may be configured according to the mode of ablation being used. Hereinbelow radiofrequency energy is assumed to be used for the ablation. The progress of the ablation can be monitored with the ultrasound imager 64.

The ablation needle 52 may have different configurations, e.g., it could comprise multiple electrodes. The needle may also have holes for irrigation.

While the ablation is performed its progress could be monitored by measuring the impedance of the ablation needle as explained above. Additionally or alternatively, the progress of the ablation may be monitored by including a temperature sensor 78 at the distal end of the probe 54 and measuring temperature at the ablation site. Further additionally or alternatively, the progress of the ablation may be monitored by evaluation of the echogenicity of the lesion using the ultrasound imager 64.

After imaging, or after the ablation, or at any other appropriate time during the procedure, in embodiments in which the balloon 66 (FIG. 4) is used, it may be deflated, enabling the collapsed segment of lung to re-expand, and the probe 54 and deflated balloon 66 may then be removed from the lung.

Reverting to FIG. 5, at some time during the procedure, typically after performance of the biopsy, it may be desirable to seal the one or more punctures that the biopsy needle 50 has made. Without sealing, the biopsy sites may bleed, so that in the case of needle biopsies within a lung section, unwanted fluid may penetrate into regions of the lung that are normally substantially liquid-free. Alternatively, an unsealed biopsy site could leak air, and even, although rarely, could act to seed cancer cells along the biopsy track (assuming the lesion is cancerous). Case reports of metastases caused by lung biopsies exist, and these metastases are probably due, at least in part, to mechanical disruption of the lesion.

Methods for sealing needle tracks are known in the art. Typically, the prior art has addressed cases where the needle track is sealed to prevent leakage of material that has been injected into tissue by the needle.

Embodiments of the present invention allow the biopsy needle 50 to apply sealant 80 to the biopsy site at the target 60. Marking material may be incorporated into the sealant, so that once the biopsy site has been sealed, its position may be more easily located and/or navigated to if subsequent inspections of the target 60 are required. The marking material may be fluorescent, so that the site is visible under fluoroscopy. Alternatively the marking material may be paramagnetic, so that the site may be located magnetically.

In some embodiments both types of marking material (fluorescent and paramagnetic) are incorporated into the sealant 80. The two types of marker allow for registration, by the lesion site itself, of a fluoroscopic imaging system with a magnetic tracking system. Registration of multimodal images may be accomplished using the teachings of commonly assigned U.S. Patent Application Publication No. 20070049817, now abandoned, which is herein incorporated by reference.

As well as sealing the biopsy site, the sealant 80 can also be used to seal the ablation site using the ablation needle or the biopsy needle. One study, Snoeren et al., *Viable Tumor Tissue Adherent to Needle Applicators after Local Ablation: A Risk Factor for Local Tumor Progression, Annals of Surgical Oncology* 18:13 (December 2011), has shown that after ablation of liver tumors, tumor tissue can remain attached to the needles applying the ablation. Consequently, in ablating lung lesions, sealing the ablation site with the type of sealant described above should reduce inadvertent spreading of possibly cancerous tumor cells.

First Alternate Embodiment

Reference is now made to FIG. 7, which is a partial view of an assembly 82 of the distal portion of an endobronchial probe in accordance with an alternate embodiment of the invention. The assembly 82 comprises hollow tubular segments 84, 86, which provide ingress for probes carrying appliances such as biopsy tools and ablation needles as described above and support for other components. For example, the segment 86 supports a balloon 88.

A deflector 90 is used to guide a needle (not shown) from the lumen of the segment 84 through an exit pore 92 on the exterior of the assembly, where it can be passed further to reach a target and used to biopsy or ablate tissue. The needle is typically hollow, in order to allow passage of irrigation fluid during the ablation to regulate the temperature of the ablation site as is known in the art. The fluid can also allow for significantly larger ablation zones using lower power than would be required without the fluid, as saline is conductive and lowers the tissue impedance. It should be noted that the deflector 90 is capable of guiding a curved needle or deflecting a straight needle. The deflector 90 typically provides a deflection angle of about 30 degrees as indicated diagrammatically by angle 94. However, the deflection angle of the deflector 90 may vary according to the geometry of the particular appliance being passed therethrough, and the deflector 90 may be constructed with a different deflection angle to accommodate the needs of a particular medical procedure. In some embodiments the deflector 90 may be removed from the assembly 82 and replaced with another deflector having a different deflection angle.

The balloon 88 is disposed distal to the deflector 90 against the segment 86, and may be positioned contralateral to, i.e., diametrically opposite the exit pore 92. When the assembly 82 is in an operating position within a bronchus, inflation of the balloon 88 urges the exit pore 92 against the bronchial wall. The balloon 88 is typically connected to a fluid source by a hydraulic line (not shown). Inflation and deflation of the balloon 88 may be accomplished manually, using liquid or gas. Alternatively, inflation and deflation of the balloon 88 may be controlled by valves in the hydraulic line or fluid source.

A push-pull anchor system comprises a plurality of movable anchor wires, of which wires 96, 98, 100 are illustrated representatively. The wires 96, 98, 100 extend from the handle 20 (FIG. 1), and each passes through a respective bore in a cylindrical member 102, and thence through a set of two elongated tubular guides, e.g., guides 104, 108. For instance, the wire 96 first passes in a distal direction through guide 104. Upon exiting the guide 104 it forms a bend 106, reversing direction to pass into guide 108 in a proximal direction. Controlled via the handle 20, the wire 96 can alternate between a first position, wherein its distal end 110 is retracted within tubular guide 108 and a second position wherein the end 110 is extended proximally beyond the guide 108 and diverges from the long axis of the segment 84 at an angle as shown in FIG. 7. The foregoing description applies in like manner to the other wires 98, 100. It will further be appreciated that while three wires are shown in FIG. 7, other embodiments may be configured with different numbers of wires and guide sets.

In the second position the outwardly extended end 110 can engage the bronchial wall and provide countertraction when an ablation or biopsy needle (not shown) is introduced through the deflector 90 and pushed into the bronchial wall. The bronchial wall may be cartilaginous or even calcified and thus may offer considerable resistance to passage of the needle. In the absence of counter-traction, the resistance would cause retrograde motion of the assembly 82.

Reference is now made to FIG. 8, which is a perspective view of the balloon 88 (FIG. 7), in accordance with an embodiment of the invention. In this view, the balloon 88 is expanded, and is configured with a longitudinal groove 112 that conforms to the segment 86 upon which it is mounted. Tubular members 114, 116 provide for ingress and egress of air or gas to expand the balloon via one or more separate lumens (not shown). The balloon 88, when expanded, surrounds most of the circumference of the segment 86 as shown in FIG. 7. Alternatively, the balloon 88 may wrap around a smaller segment of the circumference.

Reference is now made to FIG. 9, which is a partially schematic elevation of the deflector 90 (FIG. 7), shown in slight perspective, in accordance with an embodiment of the invention. As noted above, the deflector 90 is a generally cylindrical structure that attaches to the segment 84 of the assembly 82 (FIG. 7), and has a lumen 118 that communicates with the lumen of the segment 84 and can receive a biopsy or ablation needle therethrough. A bore 120 communicates with the lumen 118 and extends through the deflector 90 from the exit pore 92 to an entrance pore 122. A distal pocket 124 ends blindly and aids in affixing the deflector 90 to the distal segment 86 of the assembly 82.

The entrance pore 122 provides a second possible entrance for passage of a needle or other appliance through the deflector 90. Broken lines 126, 128 indicate alternative routes that can be taken by a tool that is inserted via the lumen 118 or via a second working channel 130 through entrance pore 122, respectively. The channel 130 is schematically demarcated by line 132. Both routes reach the exit pore 92.

Reference is now made to FIG. 10, which is an end view of the cylindrical guide member 102 (FIG. 7), shown in slight perspective, in accordance with an embodiment of the invention. A relatively large central lumen 133 allows the guide member 102 to encircle the segment 84. A plurality of relatively smaller bores 134 accommodate passage of the anchor wires, e.g., wires 96, 98, 100, as shown in FIG. 7. In this embodiment provision is made for 7 anchor wires. As noted above, different numbers of bores 134 may be provided to accommodate different numbers of anchor wires.

Reference is now made to FIG. 9, which is a partially schematic elevation of the deflector 90 (FIG. 7), shown in slight perspective, in accordance with an embodiment of the invention. As noted above, the deflector 90 is a generally cylindrical structure that attaches to the segment 84 of the assembly 82 (FIG. 7), and has a lumen 118 that communicates with the lumen of the segment 84 and can receive a biopsy or ablation needle therethrough. A bore 120 communicates with the lumen 118 and extends through the deflector 90 from the exit pore 92 to an entrance pore 122. A distal pocket 124 ends blindly and aids in affixing the deflector 90 to the distal segment 86 of the assembly 82.

A hollow needle or trocar (not shown) may be inserted through the hypotube 146. Subsequently during the procedure a biopsy or ablation probe can be introduced via the hypotube 146 or through the lumen of the hollow needle using well known techniques.

Reference is now made to FIG. 12, which is an elevation of a top plate 150 of the handle 20 (FIG. 1), in accordance with an embodiment of the invention. A longitudinal groove 152 holds the proximal end of the endobronchial probe. A transverse recess 154 in the groove 152 is adapted to contain a cylinder 155 capable of moving proximally and distally, as indicated by arrow 157. The cylinder is attached to the wires 96, 98, 100 (FIG. 7). Movement of the cylinder and the wires 96, 98, 100 thereby deploys and retracts the above-described anchor system of the assembly 82 under control of a knob 156.

Although not shown in FIG. 7, the balloon 66 (FIG. 4) may be included in the assembly 82 in order to collapse a lung segment and increase access to the target site.

In some embodiments the assembly 82 may include an integral retractable biopsy needle and at least one retractable ablation needle as described above with reference to FIG. 2, which are deployed via the deflector 90.

Second Alternate Embodiment

Figure 13:
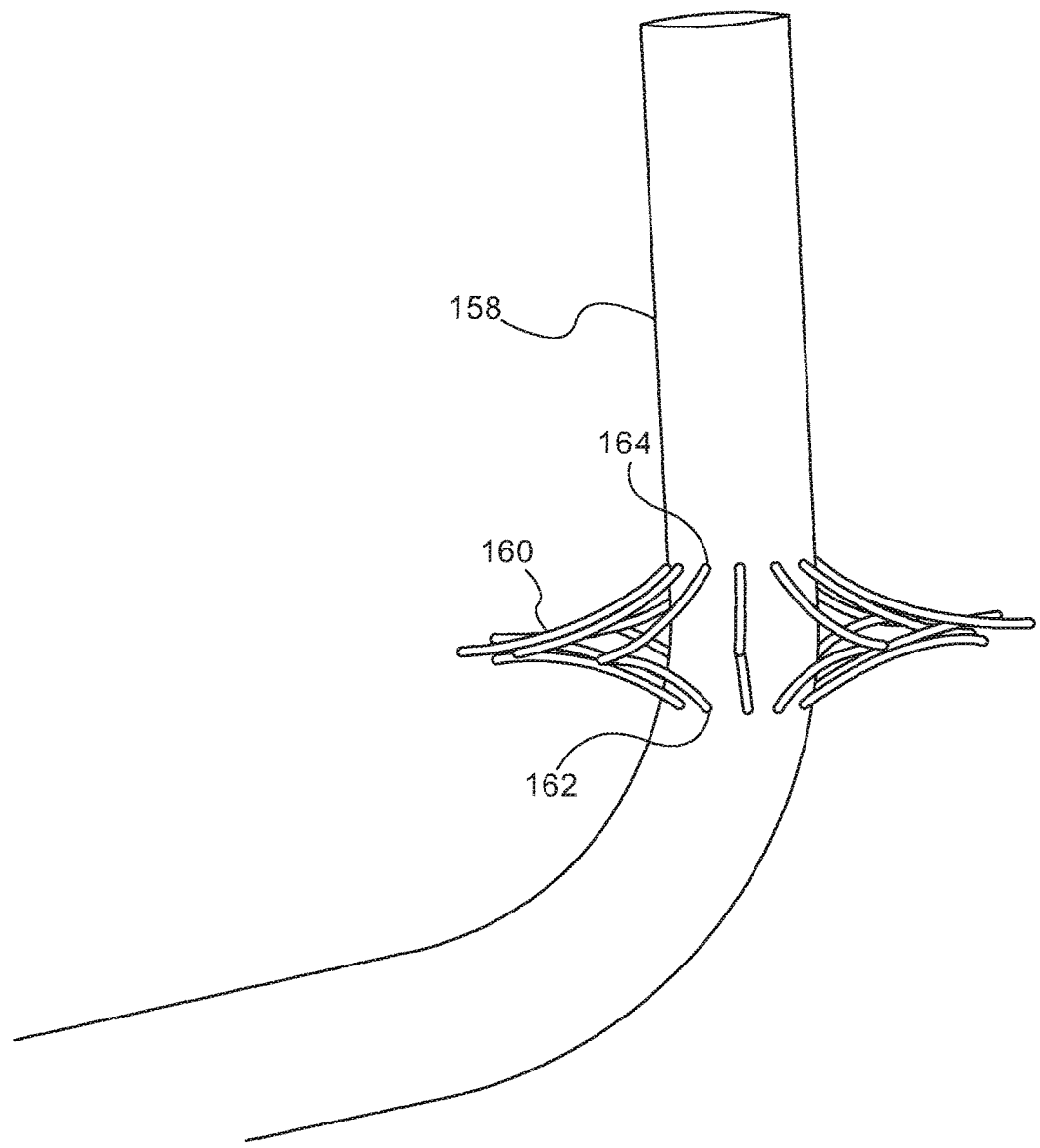
FIG. 13 is a side elevation of a shaft of an endobronchial probe in accordance with an alternate embodiment of the invention.

Reference is now made to FIG. 13, which is a side elevation of a portion of a shaft 158 of a sheath that can be placed over a wire, which was placed via the endobronchial probe through a needle, in accordance with an alternate embodiment of the invention. An anchoring assembly comprises an array of radially projecting wires 160, each exiting from the shaft 158 through two ports 162, 164. The wires 160 can be retracted, using a control on the handle 20 (FIG. 1) or extended to engage the wall of a bronchus as required during the medical procedure.

Third Alternate Embodiment

Figure 14:
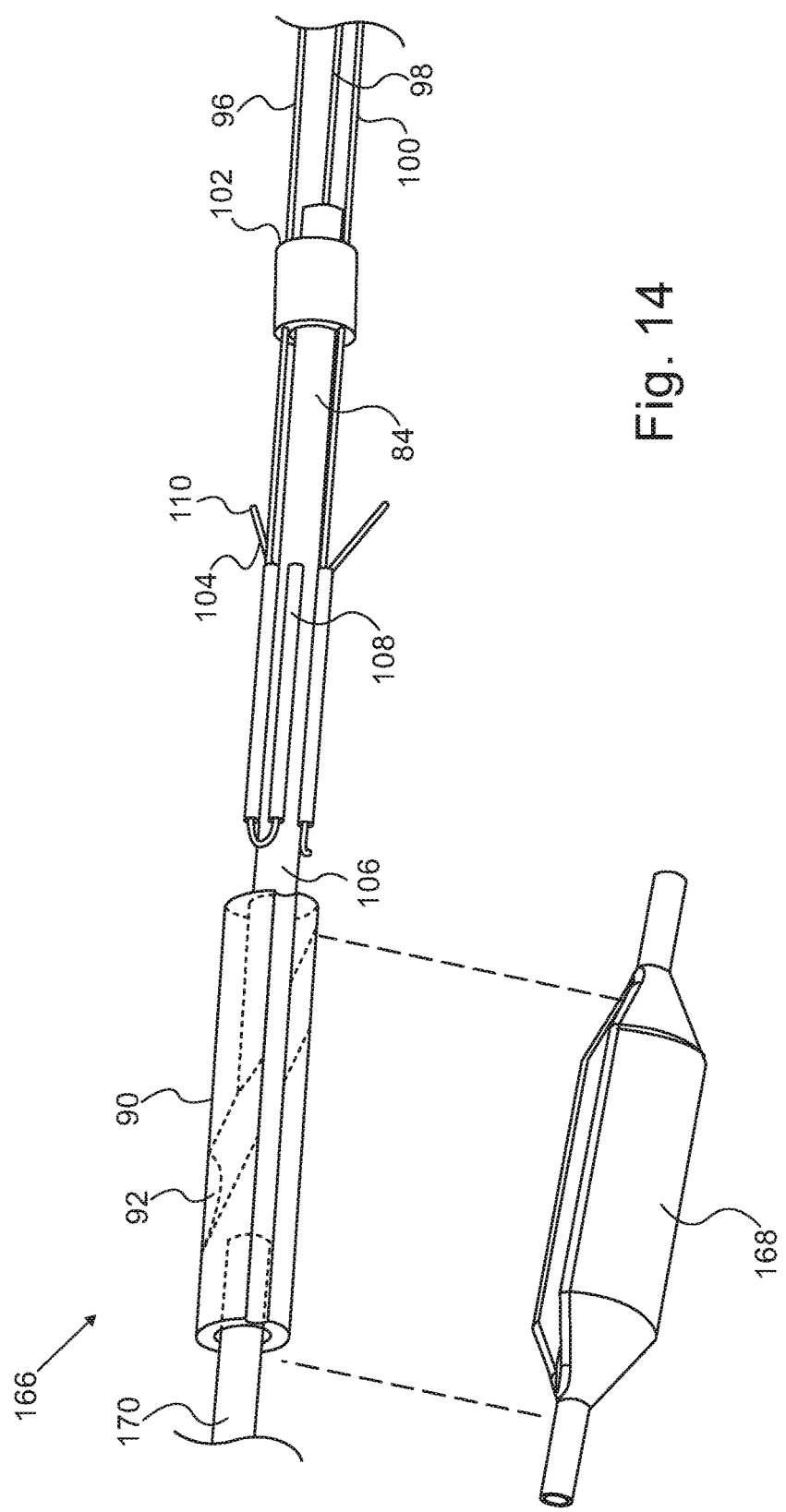
FIG. 14 is a partially exploded view of an assembly of an endobronchial probe in accordance with an alternate embodiment of the invention.

Reference is now made to FIG. 14, which is a partially exploded view of an assembly 166 of the distal portion of an endobronchial probe in accordance with an alternate embodiment of the invention. The assembly 166 is similar to the assembly 82 (FIG. 7). However, in this embodiment a balloon 168 is mounted directly over the deflector 90. When inflated it may surround a portion or most of the deflector 90, but does not obstruct the exit pore 92. A distal segment 170 may be shortened as compared with the corresponding segment 86 (FIG. 7), or may be omitted entirely. This arrangement provides a high degree of approximation of the exit pore 92 to the internal wall of a bronchus once the assembly 166 has been positioned by the operator and the balloon 168 has been inflated.

Fourth Alternate Embodiment

The description above has assumed that a needle is used for performing a biopsy, and for sealing the biopsy and/or ablation site. In alternative embodiments, the needle may be configured to perform other functions, some of which are listed below:

Brachytherapy, wherein a short-range ionizing radiation source, typically a radioisotope, may be precisely positioned at the target 60 via the biopsy needle 50. The target 60 is typically in this case a cancerous tumor. Additionally or alternatively, anti-neoplastic drugs and other ablative drugs, e.g., molecular inhibitors tailored to the tumor type or the genetic individuality of the subject can be delivered via the biopsy needle 50 to the target 60.

Positioning of a miniature dosimeter, typically in conjunction with the brachytherapy referred to above, at the target 60 The dosimeter may be a wireless or passive type.

Delivery of other injected agents, such as drugs, radiation sensitizing agents, photosensitizing agents, immunological agents and different types of cells.

Application of optical coherence tomography (OCT) for initial diagnosis of the lesion, and/or for validation of the ablation. Typically, OCT is performed using an OCT probe incorporated into the probe 54. Alternatively, OCT may be performed via one or more fiber optics passed through the biopsy needle 50.

Positioning of a thermal probe, typically for thermography to validate the ablation. Alternatively, the ablation may also be validated by operating the ultrasound imager in an acoustic radiation force impulse imaging (ARFI) mode, in which case the thermal probe may be omitted.

While the probe described herein is configured for a transbronchial procedure, it may also be used during a combined transbronchial-transthoracic procedure.

Consideration of the description above indicates that embodiments of the present invention are suitable for volumetric analysis of the lesion, application of ablation or other procedures according to the lesion volume, and utilization of the biopsy needle according to the lesion volume. Such a volumetric approach enables simulation and planning of a personal therapeutic procedure, as well as prediction of the outcome of the procedure. Such volumetric procedures include, but are not limited to, determination of the volume of ablated tissue. Data for the volumetric analysis may be provided by the ultrasound imager 46 (FIG. 2). Techniques for volumetric analysis of lesions are known, e.g., from the documents Gavrielides et al, *Noncalcified Lung Nodules: Volumetric Assessment with Thoracic CT, Radiology: Volume* 251:1, April 2009, and Mozley et al., *Measurement of Tumor Volumes Improves RECIST-Based Response Assessments in Advanced Lung Cancer, Translational Oncology*, 5:1, pp 19-25, February 2012.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method of endoscopy comprising the steps of:
    (a) inserting into a bronchus of a lung an elongated assembly having a lumen, a long axis, a separate channel extending alongside with the lumen, a distal segment, and a deflector disposed in the distal segment, the lumen extending generally along the long axis, the deflector having a proximal end defining a first entrance pore in communication with the lumen, a second entrance pore located distally from the first entrance pore, and an exit pore, wherein the second entrance pore is in communication with the separate channel, the deflector defining a bore in communication with the first entrance pore, the second entrance pore, and the exit pore, the bore extending therethrough at an angle to the long axis, wherein the exit pore is laterally oriented relative to the lumen;
    (b) introducing a tool into the deflector via either the first entrance pore or the second entrance pore;
    (c) transmitting signals from a location sensor disposed in the distal segment to a position processor that is operative for computing a location of the distal segment responsively to the signals from the location sensor;
    (d) imaging a target in the lung using an ultrasound imager disposed in the distal segment and transmitting data provided by the ultrasound imager to electronic circuitry for processing thereof;
    (e) urging the exit pore of the deflector laterally against a wall of the bronchus by inflating an inflatable balloon disposed on the distal segment, wherein the inflatable balloon is positioned contralateral to the exit pore, wherein the inflatable balloon defines a longitudinally extending groove, wherein the elongated assembly further comprises a tubular segment laterally received in the longitudinally extending groove;

(f) thereafter penetrating the wall of the bronchus with the tool via the exit pore, as the exit pore is urged against the wall of the bronchus by the inflated inflatable balloon, to reach the target in the lung with the tool;

(g) anchoring the assembly to provide counter-traction thereon while penetrating the wall of the bronchus using a push-pull anchoring system comprising a plurality of guides and respective wires threaded therethrough by moving the wires between a first position wherein the wires are retracted within the guides and a second position wherein the wires extend beyond the guides and diverge from the long axis sufficiently to engage the wall of the bronchus; and (h) performing an operation on the target using the tool.

2. The method according to claim 1, wherein introducing the tool comprises passing the tool through the lumen such that the deflector deflects a distal portion of the tool laterally relative to the lumen and out through the exit pore.

3. The method according to claim 1, wherein the assembly further comprises a proximal segment and a handle having a wire control disposed on the proximal segment, wherein anchoring the assembly comprises moving the wires by activating the wire control.

4. The method according to claim 1, wherein the location sensor is a tri-axial magnetic field sensor.

5. The method according to claim 1, wherein the location sensor is an electrode that reports impedance measurement signals to the position processor cooperatively with a plurality of body surface electrodes.

6. The method according to claim 1, wherein the inflatable balloon is positioned distally in relation to the exit pore.

7. The method according to claim 1, wherein the longitudinally extending groove is angularly positioned to correspond with an angular position of the exit pore in relation to the long axis, thereby positioning the inflatable balloon contralaterally relative to the exit pore.

8. The method according to claim 1, wherein each wire exits through a respective pair of ports, wherein each pair of ports comprises a first port and a corresponding second port.

9. The method according to claim 8, wherein each first port is positioned distally in relation to the corresponding second port.

* * * * *